United States Patent [19]  
Wang et al.

[11] Patent Number: 4,714,468  
[45] Date of Patent: Dec. 22, 1987

[54] PROSTHESIS FORMED FROM DISPERSION STRENGTHENED COBALT-CHROMIUM-MOLYBDENUM ALLOY PRODUCED BY GAS ATOMIZATION

[75] Inventors: Kathy K. Wang, Suffern, N.Y.; Larry J. Gustavson, Dover; John H. Dumbleton, Ridgewood, both of N.J.

[73] Assignee: Pfizer Hospital Products Group Inc., New York, N.Y.

[21] Appl. No.: 7,064

[22] Filed: Jan. 27, 1987

Related U.S. Application Data

[62] Division of Ser. No. 765,298, Aug. 13, 1985.

[51] Int. Cl.[4] .................. B22F 1/00; C22C 19/07; C22C 29/12
[52] U.S. Cl. ........................... 623/16; 623/23; 75/235; 419/19; 419/28; 148/408; 420/436; 420/437; 420/439
[58] Field of Search ............... 623/16, 23; 75/235; 419/19, 28; 148/408; 420/436, 437, 439

[56] References Cited

U.S. PATENT DOCUMENTS 3,356,542 12/1967 Smith .................... 148/408
3,591,362 7/1971 Benjamin ............... 75/251
3,649,256 3/1972 Fletcher ................. 420/436
3,865,585 2/1975 Rademacher ........... 420/436
4,012,229 3/1977 Herchenroeder et al. ... 420/436

FOREIGN PATENT DOCUMENTS 2350546 4/1974 Fed. Rep. of Germany ...... 420/436
423562 2/1935 United Kingdom ............. 420/438
974185 11/1964 United Kingdom ............. 420/438
368341 1/1973 U.S.S.R. ....................... 420/436

OTHER PUBLICATIONS

Gessinger, *Powder Metallurgy of Superalloys*, Butterworths, Boston Mass., (1984), p. 22.
Klar et al, "Atomization", Metals Handbook, 9th Ed., vol. 7, 1984, pp. 25–38.

*Primary Examiner*—John F. Terapane
*Assistant Examiner*—Eric Jorgensen
*Attorney, Agent, or Firm*—Peter C. Richardson; Lawrence C. Akers; Mark Dryer

[57] ABSTRACT

A dispersion strengthened cobalt-chromium-molybdenum alloy produced by gas atomization containing a fine oxide dispersion, and characterized, after fabrication by gas atomization, thermomechanical processing and further high temperature exposure, by excellent corrosion resistance, high fatigue strength, high ductility and high temperature stability; a process for producing said alloy and prostheses formed from said alloy.

6 Claims, 1 Drawing Figure

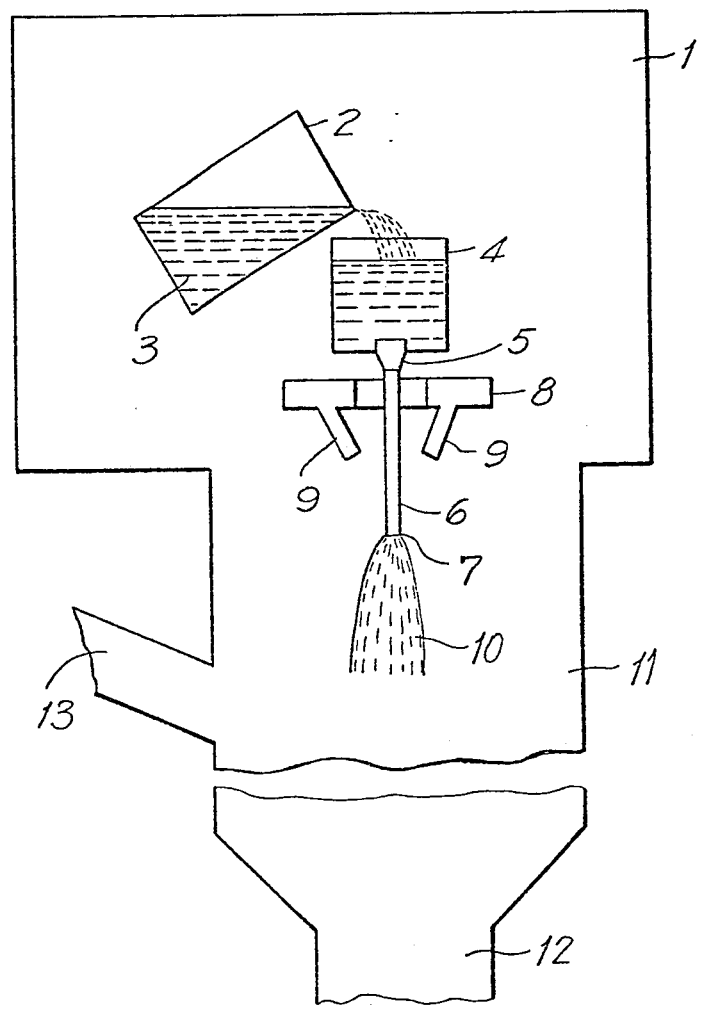

PROSTHESIS FORMED FROM DISPERSION STRENGTHENED COBALT-CHROMIUM-MOLYBDENUM ALLOY PRODUCED BY GAS ATOMIZATION

This is a division of application Ser. No. 765,298, filed on Aug. 13, 1985.

BACKGROUND OF THE INVENTION

This invention relates to a cobalt-based alloy containing a substantial proportion of chromium and molybdenum together with other alloying ingredients, particularly ingredients which provide a fine oxide dispersion, said alloy being produced by a gas atomization process. The invention is also concerned with a process for producing said alloy and to prostheses formed therefrom.

The alloy of the present invention falls within a class known in the art as "superalloys".

The term "superalloy" is a term of art which generally signifies an alloy having particularly high strength, good mechanical and corrosion-resistant characteristics and a stable microstructure. Of particular interest are those alloys which additionally retain high strength properties (and stable microstructures) following thermal treatments at extremely high temperatures.

The known Vitallium ® alloy is a high corrosion-resistant cobalt/chromium alloy which is used successfully in numerous orthopaedic applications. A typical composition for Vitallium ® alloy is the following:

| Element | % by weight |
|---|---|
| Carbon | 0.25 |
| Silicon | 0.75 |
| Manganese | 0.70 |
| Chromium | 28.00 |
| Molybdenum | 5.50 |
| Cobalt | 64.80 |

Because of its many favorable properties, for example, high ambient temperature strength and fatigue strength, resistance to wear, bio-compatibility and particularly corrosion resistance, Vitallium ® alloy is used extensively in orthopaedic applications, especially for prostheses. A particularly useful development in the area of orthopaedic implants is the provision of a porous coating in the form of multiple layers of spherical Vitallium ® alloy particles on the surface of a Vitallium ® alloy for the enhancement of implant fixation. However, with the advent of porous coating, some of the fatigue strength of cast Vitallium ® alloy may be lost due to the elevated temperature required for sintering. Accordingly, there is a need to provide a Vitallium ®-type alloy for hip implants wherein the fatigue strength is maximized.

It is known that the properties of a given metal alloy are dependent upon its composition and also upon the manner in which the various alloying ingredients are formed into the final alloy. One method of alloy formation is known as "mechanical alloying" and this method ideally produces homogeneous composite particles with a uniformly dispersed oxide. The process is described in an article entitled "Dispersion Strengthened Superalloys by Mechanical Alloying" by John S. Benjamin, Metallurgical Transactions, Vol. 1 October 1970, p. 2943.

U.S. Pat. No. 3,591,362, issued July 6, 1971 to John S. Benjamin discloses a composite alloy powder formed by the technique of mechanical alloying.

The inclusion of certain selected oxides in the alloy composition can improve the properties of the final alloy and oxide dispersion strengthened (O.D.S.) superalloys made by the mechanical alloying process exhibit high-temperature strength and stability as a result of the presence of stable oxide dispersions which resist thermal damage and permit much greater freedom in alloy design.

Patent Application Ser. No. 703352, filed Feb. 20, 1985 discloses an improved cobalt-chromium superalloy made in accordance with O.D.S. mechanical alloying procedures which has not only the high corrosion-resistant properties typical of Vitallium ® alloy but also excellent room temperature strength (tensile and fatigue) properties which are substantially retained after exposure to severe thermal conditions.

While the improved alloy of Application Ser. No. 703352 has excellent strength properties and high temperature stability which makes it vastly superior to any prior art alloy, said improved alloy has insufficient ductility for conventional hot working.

Surprisingly, it has now been found that an alloy having greatly enhanced ductility and consequential good hot workability, may be obtained when the alloy, having small amounts of oxides and nitrides, is produced by gas atomization and suitable thermomechanical processing rather than the mechanical alloying procedure described above.

Gas atomization of metals is a known technique for producing alloy powders having certain powder characteristics such as average particle size, particle-size distribution and particle shape. These characteristics affect the mechanical properties of the solid alloy which is formed by consolidating the powder. Typical methods of gas atomization are described in the literature; for example, ASM Handbook 9th edition, Vol. 7 Powder metallurgy p. 25-38, American Society for Metals, Metals Park Ohio, 1984.

SUMMARY OF THE INVENTION

Accordance with the present invention there is provided a high strength, corrosion-resistant, high temperature stable consolidated, biocompatible ductile alloy having homogeneously distributed dispersed oxides and fine, equiaxed grain structure after high temperature exposure, produced by gas atomization and consisting essentially of the following percentage composition by weight:

| | |
|---|---|
| chromium | 26 to 30 |
| molybdenum | 5 to 7 |
| manganese | 0 to 1 |
| silicon | 0 to 1 |
| iron | 0 to 0.75 |
| nickel | 0 to 1.0 |
| carbon | 0 to 0.35 |
| nitrogen | 0 to 0.25 |
| oxygen | 0.003 to 0.20 |
| oxide-forming metal | 0.03 to 2.0 | and the balance cobalt, apart from trace amounts of incidental impurities; in which the oxide-forming metal is a metal selected from the group consisting of magnesium, calcium, aluminum, yttrium, lanthanum, titanium and zirconium, which forms high temperature-stable, non-accretive, fine oxide particles which oxide has a free energy of formation greater than the oxide of the matrix metal and is homogeneously distributed in the dispersed phase; and said alloy after fabrication by gas atomization, thermomechanical processing and further high temperature exposure has an ultimate tensile strength of 1103–1379 MPa (160–200 ksi), a 0.2% offset yield strength of 517–690 MPa (75–100 ksi), an elongation of 37 to 60%, and a fatigue strength at $10^7$ cycles (Rotating Beam) of 483–655 MPa (70–95 ksi).

As used herein, the expression "trace amounts of incidental impurities" is intended to mean those materials which are unavoidably retained in minute amounts whatever the degree of purification of the desired alloy ingredients, but whose presence does not materially affect the properties of the final alloy.

As used herein the term "thermomechanical processing" means the high temperature processing steps known in the art for consolidating and forming alloys. These steps include extrusion, swaging and forging. The term "high temperature exposure" means exposure to temperatures above the recrystallization temperature of the alloy, such as those temperatures used during hot working, including not only the aforementioned thermomechanical processing but also any subsequent sintering steps.

The invention also provides a process for producing a high temperature stable, consolidated, biocompatible, ductile alloy having homogeneously distributed dispersed oxides and fine, equiaxed grain structure after high temperature exposure, which comprises melting under an atmosphere consisting substantially of nitrogen, an inert gas or a mixture thereof an alloy mixture consisting essentially of the following percentage composition by weight:

| chromium | 26 to 30 |
| molybdenum | 5 to 7 |
| manganese | 0 to 1 |
| silicon | 0 to 1 |
| iron | 0 to 0.75 |
| nickel | 0 to 1.0 |
| carbon | 0 to 0.35 |
| nitrogen | 0 to 0.25 |
| oxygen | 0.003 to 0.20 |
| oxide-forming metal | 0.03 to 2.0 | and the balance cobalt, apart from trace amounts of incidental impurities, said oxide-forming metal being a metal selected from the group consisting of magnesium, calcium, aluminum, yttrium, lanthanum, titanium and zirconium, which forms high temperature-stable, non-accretive, fine oxide particles which oxide has a free energy of formation greater than the oxide of the matrix metal and being homogeneously distributed in the dispersed phase, wherein the cobalt, chromium, molybdenum and carbon are charged first, the resulting charge is flooded with nitrogen and/or inert gas and melted at a temperature within the range of 1454° C. (2650° F.) to 1538° C. (2800° F.), the manganese and silicon are then added, while maintaining the temperature of the molten mixture below 1510° C. (2750° F.), followed by addition of the oxide-forming metal, which acts as a getter for oxygen present in the original mixture and thus providing dispersed oxide, the nitrogen being present as nitride, immediately subjecting the molten mixture to gas atomization to produce an alloy powder containing a fine oxide dispersion homogeneously distributed throughout the alloy and then thermomechanically processing said alloy powder to provide an alloy having an ultimate tensile strength of 1103–1379 MPa (160–200 ksi), a 0.2% offset yield strength of 517–690 MPa (75–100 ksi), an elongation of 37 to 60%, and a fatigue strength at $10^7$ cycles (Rotating Beam) of 483–655 MPa (70–95 ksi).

The invention further provides a prosthesis made by forging a high-strength, corrosion-resistant, high temperature stable, ductile alloy having fine, equiaxed grain structure after high temperature exposure, produced by gas atomization and having a percentage composition by weight as described above. The actual procedure for making the prosthesis is preferably a standard forging process such as that conventionally used in the production of hip stems. A particularly preferred embodiment of the invention is a prosthesis made as described and having a porous coating. An example of a typical prosthesis is an artificial hip.

The oxide which provides the fine oxide dispersion in the ODS alloy produced by the process of the invention is a refractory oxide which has a free energy of formation greater than the oxide of the matrix metal, i.e. the cobalt-chromium-molybdenum base metal.

Additionally the oxide must be adapted to form non-accretive fine particles in the dispersed phase. Examples of suitable refractory oxides are the oxides of magnesium, calcium, aluminum, yttrium, lanthanum, and titanium, zirconium. The preferred refractory oxide-forming metals are aluminum, lanthanum and yttrium. Particularly preferred alloys of the invention are those in which the oxide-forming metal is aluminum, lanthanum or a mixture thereof.

The presence of the fine oxide dispersion strenthens the alloy and fabrication by gas atomization and thermochemical processing enhances the ductility. The resultant improved alloy is referred to herein as gas atomized dispersion strengthened (GADS) alloy.

A preferred embodiment of the invention is a high strength, corrosion-resistant, high temperature stable, ductile GADS alloy as described above in which the percentage composition by weight is:

| chromium | 26.47–27.27 |
| molybdenum | 5.50–6.01 |
| manganese | 0.73–0.78 |
| silicon | 0.70–0.71 |
| iron | 0.066–0.520 |
| nickel | 0.002–0.187 |
| carbon | 0.09–0.11 |
| nitrogen | 0.10–0.25 |
| oxygen | 0.0035–0.016 |
| aluminum | 0.40–0.81 |
| lanthanum | 0–0.15 | and the balance cobalt, apart from trace amounts of incidental impurities.

A particularly preferred species of the invention is a GADS alloy in which the percentage composition by weight is:

| chromium | 27.24 |
| molybdenum | 5.97 |
| manganese | 0.74 |
| silicon | 0.71 |
| iron | 0.215 |
| nickel | 0.053 |
| carbon | 0.09 |
| nitrogen | 0.21 |
| oxygen | 0.0038 |

| -continued | |
|---|---|
| aluminum | 0.045 |
| lanthanum | 0.022 | and the balance cobalt, apart from trace amounts of incidental impurities, and said alloy after fabrication by gas atomization, thermomechanical processing and further high temperature exposure has an elongation of 58.7%.

Another preferred species in a GADS alloy in which the percentage composition by weight is:

| | |
|---|---|
| chromium | 26.81 |
| molybdenum | 5.97 |
| manganese | 0.74 |
| silicon | 0.70 |
| iron | 0.52 |
| nickel | 0.094 |
| carbon | 0.09 |
| nitrogen | 0.22 |
| oxygen | 0.0142 |
| aluminum | 0.47 |
| lanthanum | 0.15 | and the balance cobalt, apart from trace amounts of incidental impurities, and said alloy after fabrication by gas atomization, thermomechanical processing and further high temperature exposure has an elongation of 51.0%.

DETAILED DESCRIPTION OF THE INVENTION

The high strength, corrosion-resistant, high temperature stable, ductile GADS alloy of the invention is produced in powder form by gas atomization and the resulting powder is consolidated by thermomechanical processing to provide a solid alloy which may be worked, for example, by forging, to form a prosthesis.

Gas atomization is carried out by melting the desired alloy ingredients, for example, by induction melting, under an atmosphere consisting substantially of nitrogen, an inert gas or a mixture thereof. Preferably the induction melting is carried out under a nitrogen atmosphere. The alloy ingredient are charged to the mixture in the sequence described hereinabove. The molten mix is then gas atomized according to a gas atomization procedure known in the art.

A suitable apparatus for performing the gas atomization is illustrated schematically in the accompanying drawing.

BRIEF DESCRIPTION OF THE DRAWING

The accompanying drawing is a schematic cross-section representation of an apparatus suitable for carrying out a gas atomization process according to the invention.

The apparatus illustrated in the drawing comprises a melt chamber 1, which contains a furnace 2 in which the alloy ingredients are melted under a nitrogen atmosphere to form a molten mixture 3. The melt from the furnace is poured into a tundish 4 from which the flow of the molten mixture is controlled through a nozzle 5 into a teeming stream 6 terminating in an atomization zone 7. The atomization of the molten metal is achieved with the aid of an inert gas, for example nitrogen, fed through a plenum 8 and delivered under high pressure, for example from 700-750 p.s.i., through jets 9 to the atomization zone where it atomizes the molten alloy into a homogeneous powder 10 which descends as a fine particle curtain in vertical tower 11 to a liquid nitrogen cooled collector car 12 at the base of the tower. The gas exits through a gas exhaust pipe 13 in the side wall of the vertical tower.

DESCRIPTION OF PREFERRED EMBODIMENTS

The following examples and experimental results illustrate the preparation and testing of GADS alloys in accordance with the present invention.

EXAMPLE 1

A 150 lb mixture of alloying ingredients to give an alloy having the following percentage composition by weight:

| | |
|---|---|
| chromium | 26.47 |
| molybdenum | 5.5 |
| manganese | 0.78 |
| silicon | 0.71 |
| aluminum | 0.40 |
| nickel | 0.002 |
| iron | 0.066 |
| carbon | 0.09 |
| oxygen | 0.016 |
| nitrogen | 0.10 |
| lanthanum | 0.04 |
| cobalt | balance | was induction melted under a nitrogen atmosphere according to the following procedure.

The cobalt, chromium, molybdenum and carbon raw ingredients were charged into the furnace (see drawing). It is to be noted iron and nickel which appear in the final analysis of the composition are not deliberate additions but are always present in minor amounts in alloys containing cobalt and chromium. In the alloys of the present invention, particularly those adapted to be used in prostheses, the nickel content is kept as low as possible.

The furnace containing the above charge was evacuated to a pressure of 250 μm and was then flooded with nitrogen at 0.5 atmosphere.

The alloy powder was induction melted at a temperature of 1482° C. (2700° F.)

The manganese and silicon ingredients were added to the melt.

The temperature of the melt was checked and maintained below about 1510° C. (2750° F.).

The aluminum and lanthanum were added to the melt.

Immediately after the aluminum and lanthanum were melted in the alloy mixture the molten mixture was poured into the tundish (see drawing) whence the melt was conveyed through the nozzle and atomized with argon gas at a pressure of about 700 p.s.i.

After screening to remove the coarse +60 mesh particles, the gas atomized powder prepared above was packed into mild steel cans, which were then evacuated at 204° C. (400° F.) to a leak rate of 10 micron/minute and sealed. The alloy was then extruded in a 1400 ton press at a temperature of 1121° C. (2050° F.) or 1177° C. (2150° F.) with an extrusion ratio of 9:1. In each case the billets were heated four hours at the extrusion temperature prior to extrusion. Lubrication was by oil-base graphite. No problems were encountered during extrusion at either temperature. The size of the extruded bar in each case was 38.1 mm (1.5 in.) diameter, including the mild steel can material. The extruded bars were then pickled to remove the can material to prepare for hot working.

Following extrusion the bars were subjected to hot swaging and forging to evaluate the hot workability of the alloy.

The alloy was processed through the same sequence of operations currently employed in producing forged hip stem prostheses from forged strength (FHS®) Vitallium® alloy.

The extruded bar was cut into two substantially equal pieces about 22 inches long and each was swaged at about 1066° C. (1950° F.) and 1121° C. (2050° F.), respectively, after preheat for 0.5 hour at 871° C. (1600° F.) and one hour at the swaging temperature. The extruded bar were swaged from 34.9 mm (1.375 in.) using four passes: 31.7 mm (1.248 in.), 27.7 mm (1.089 in.), 23.6 mm (0.929 in.) and then to 21.0 mm (0.825 in.) with reheat after each pass.

The 1066° C. (1950° F.) and 1121° C. (2050° F.) swaged bars were forged at 1066° C. (1950° F.) and 1121° C. (2050° F.), respectively, using the standard hip stem prostheses forging practice for FHS® Vitallium® alloy.

Composition of the alloy powder and metallographic and strength characteristics of the forged alloy were evaluated and the results determined according to the following procedures.

The percentage composition of the GADS alloy powder is given above. The major alloying element contents are within the range of ASTM F799-82 specification which gives the following chemical composition limits for cobalt-chromium-molybdenum alloys used in the production of surgical implants:

|  | Chemical Requirements Composition, % | |
|---|---|---|
|  | min | max |
| Chromium | 26.0 | 30.0 |
| Molybdenum | 5 | 7 |
| Nickel | — | 1.0 |
| Iron | — | 1.5 |
| Carbon | — | 0.35 |
| Silicon | — | 1.0 |
| Manganese | — | 1.0 |
| Nitrogen | — | 0.25[A] |
| Cobalt[B] | balance | |

[A]If N < 0.10, content does not have to be reported.
[B]Approximately equal to the difference between 100% and the sum percentage of the other specified elements. The percentage of cobalt by difference is not required to be reported.

The differences in composition between the alloy of Example 1 and the conventional FHS Vitallium are the presence of aluminum and lanthanum, and the low nickel content. The aluminum and lanthanum, the oxide-forming elements, were intentionally added to the molten mixture prior to atomization. The low nickel content was achieved by careful selection of raw materials. The nitrogen content was somewhat lower than the desired optimum (about 0.22%) and this was due to the unexpected nitrogen loss through argon atomization. In subsequent Examples the nitrogen content was maintained within the weight range of 0.21 to 0.26% by using nitrogen atomization.

The screen analysis of the gas atomized powder was as follows:

| Screen Analysis, Mesh Size (U.S. Standard) % | | | | | |
|---|---|---|---|---|---|
| +30 | −30/60 | −60/100 | −100/200 | −200/325 | −325 |
| 12 | 28 | 30 | 16 | 8 | 6 |

The actual −60 mesh powder yield was about 55% from the 150 pound original raw material charge.

Microstructure examination of the powder revealed spherical particles with dendritic structure.

The GADS alloy was successfully consolidated by extrusion and thermomechanically processed by swaging and forging to the final forged hip stems. This indicates that the alloy has good workability.

To observe the grain structure, microstructure examinations were conducted on forged hip stems in as-forged, sinter cycle [2 h/1218° C. (2225° F.)+0.5 h/1293° C. (2360° F.)] and [(2 h/1218° C. (2225° F.)+0.5 h/1343° C. (2450° F.)] treated conditions. The metallographic samples were etched in 95% hydrochloric acid and 5% hydrogen peroxide (30%).

The microstructure of the as-forged GADS alloy was compared with those of cast and FHS® Vitallium® alloy. Both GADS and FHS® Vitallium® alloy exhibited a fine, equiaxed grain structure, ASTM #10 and 9, respectively containing deformation twins indicative of the recrystallization the alloy undergoes during hot working. In contrast, the cast alloy has a very coarse dendritic structure characteristic of investment casting.

After a sinter cycle heat treatment the difference between the three alloys becomes most significant. Both the FHS® Vitallium® alloy and cast Vitallium® alloy undergo dramatic microstructural changes following exposure to the sintering temperature while the GADS alloy remains virtually unchanged.

The GADS alloy still exhibited a fine, equiaxed grain structure, (ASTM #8), however significant grain growth occurred in the FHS® Vitallium® alloy (ASTM #1). As to the cast Vitallium® alloy, the dendritic carbides which strengthen the cast material were either dissolved or incipiently melted.

Study also showed that the GADS alloy could be annealed at 1343° C. (2450° F.) with no significant grain structure changes. These results indicate that this alloy is thermally stable. This is due to the oxide and nitrides acting as inhibitors to grain growth.

No significant grain structure difference was observed between the 1066° C. (1950° F.) and 1121° C. (2050° F.) forged GADS alloy.

Cantilever bend fatigue tests were performed in the as-forged, sinter cycle treated and porous coated conditions. This testing was done in air at 30 HZ on either a Sonntag or ESH fatigue machine at A=1. The results are set out in the following table I:

TABLE I

| | Cantilever Fatigue Properties of GADS Alloy | | | | | |
|---|---|---|---|---|---|---|
| | Specimen | | Stress | | Cycles | |
| Alloy | Number | Condition | MPa | (ksi) | × 10³ | Results |
| GADS | 1[(1)] | Sinter | 621 | (90) | 10,200 | RO[(3)] |
| | | Sinter | 758 | (110) | 10,300 | RO[(3)] |
| | | Sinter | 896 | (130) | 1,990 | Specimen bent |
| GADS | 2[(2)] | Sinter | 1103 | (160) | 22 | Failed |

TABLE I-continued

Cantilever Fatigue Properties of GADS Alloy

| Alloy | Specimen Number | Condition | Stress MPa | (ksi) | Cycles × 10³ | Results |
|---|---|---|---|---|---|---|
| GADS | 3⁽²⁾ | Sinter | 896 | (130) | 2,000 | Failed |
| GADS | 4⁽²⁾ | Sinter | 827 | (120) | 15,200 | RO⁽³⁾ |
| GADS | 5⁽¹⁾ | Sinter | 862 | (125) | 10,000 | RO⁽³⁾ |
|  |  | Sinter | 931 | (135) | 15,300 | RO⁽³⁾ |
|  |  | Sinter | 1034 | (150) | 239 | Failed |
| Cast Vitallium ® Alloy |  | Sinter | 414 | (60) | 10,000 | RO⁽³⁾⁽⁴⁾ |
| FHS ® Vitallium ® Alloy |  | Sinter | 414 | (60) | 10,000 | RO⁽³⁾⁽⁴⁾ |
| GADS | 6⁽¹⁾ | Porous Coated | 621 | (90) | 199 | Failed |
| GADS | 7 | Porous Coated | 483 | (70) | 10,000 | RO⁽³⁾ |
| Cast Vitallium ® Alloy |  | Porous Coated | 276 | (40) | 10,000 | RO⁽³⁾⁽⁴⁾ |

Note:
⁽¹⁾Testing was done on SONNTAG (open loop electromechanical fatigue tester
⁽²⁾Testing was done on ESH (closed loop serve hydravlic fatigue tester
⁽³⁾RO = run out (no failure up to 10⁷ cycles)
⁽⁴⁾Fatigue limit.
Specimens No. 1 and 6 were forged at 2050° F.
Specimens No. 2, 3, 4 and 5 were forged at 1950° F.
The above data indicate that the GADS alloy is stronger than (approximately twice) cast and FHS ® Vitallium ® alloy in the sintered condition.
Rotating beam fatigue tests were performed in both as-forged and sinter cycle treated conditions. The data are given in the following Table II: -

TABLE II

Krouse Rotating Beam Fatigue Properties Of GADS Alloy

| Alloy | Specimen Number | Condition | Stress MPa | (ksi) | Cycles × 10³ | Results |
|---|---|---|---|---|---|---|
| GADS | 1 | as forged | 690 | (100) | 13,409 | RO⁽³⁾ |
| GADS | 1⁽¹⁾ | as forged | 827 | (120) | 120 | GSF⁽⁴⁾ |
| GADS | 2 | as forged | 758 | (110) | 6,375 | GSF⁽⁴⁾ |
| GADS | 3 | as forged | 896 | (130) | 73 | GSF⁽⁴⁾ |
| Cast Vitallium ® Alloy | — | Solution heat treated⁽²⁾ | 414 | (60) | 10,000 | RO⁽³⁾⁽⁵⁾ |
| FHS Vitallium ® Alloy | — | as forged | 758 | (110) | 10,000 | RO⁽³⁾⁽⁵⁾ |
| GADS Alloy | 4 | Sinter | 621 | (90) | 92 | GSF⁽⁴⁾ |
| GADS | 5 | Sinter | 621 | (90) | 94 | GSF⁽⁴⁾ |
| GADS | 6 | Sinter | 483 | (70) | 8,149 | GSF⁽⁴⁾ |
| GADS | 7 | Sinter | 448 | (65) | 16,804 | RO⁽³⁾ |
| GADS | 7⁽¹⁾ | Sinter | 483 | (70) | 10,265 | GSF⁽⁴⁾ |
| Cast Vitallium ® Alloy | — | Sinter | 276 | (40) | 10,000 | RO⁽³⁾⁽⁵⁾ |
| FHS Vitallium ® Alloy | — | Sinter | 324 | (47) | 10,000 | RO⁽³⁾⁽⁵⁾ |

Note:
⁽¹⁾This test was conducted with a specimen which had run out at a lower stress level
⁽²⁾one hour at 1218° C. (2225° F.)
⁽³⁾RO = run out (no failure up to 10 million cycles)
⁽⁴⁾GSF = gage section failure
⁽⁵⁾Fatigue limit.
Specimens No. 1, 2, 6 and 7 were forged at 1066° C. (1950° F.)
Specimens No. 3, 4, 5 were forged at 1121° C. (2050° F.)

Comparison of the above data with data obtained for FHS ® Vitallium ® alloy and cast Vitallium ® alloy indicate that the as-forged GADS alloy is comparable in fatigue strength to the FHS ® Vitallium ® and stronger than cast Vitallium ® alloy. In the sintered condition the GADS alloy is much stronger than the case and FHS ® Vitallium ® alloy, which agrees with data obtained in the cantilever fatigue tests.

In the porous coated condition, the fatigue strength of the GADS alloy (483 MPa (70 ksi) at 10⁷ cycles) is also much higher than that of cast Vitallium ® alloy (276 Mpa (40 ksi) at 10⁷ cycles). This corresponds to an approximately 75% strength improvement over prior art hip prostheses. From the available data, the fatigue properties of GADS alloy forged at 1066° C. (1950° F.) are comparable to those of GADS alloy forged at 1121° C. (2050° F.).

To determine the excellent corrosion resistance of the GADS alloy, anodic polarization tests were conducted in deaerated 0.9% sodium chloride at 37° C. on smooth samples in the sinter cycle treated condition. FHS ® and cast Vitallium ® alloy were also tested in the same condition as a reference. Samples were scanned from their free corrosion potential to +700 mv (a potential region of oxide film damage) then the scan was reversed until evidence of film repair was seen. The free corrosion potentials (Ecorr) and pitting protection potentials (Ep) were measured for each alloy.

The average anodic polarization scans (potential vs normalized current) of the GADS alloy were almost identical with those of cast and FHS ® Vitallium ® alloy. A small hysteresis was seen in each of these three materials during reverse scan which indicates effective film repair.

The free corrosion potential (Ecorr) and pitting protection potential (Ep) are summarized in the following Table III. All potentials are given relative to the saturated calomel electrode.

TABLE III

Anodic Polariztion Corrosion Resistance Of GADS Alloy Compared To Cast And FHS Vitallium ® Alloy
Condition: 0.9% NaCl at 37° C.

|  | E(corr (mv) | Ep (mv) |
|---|---|---|
| GADS Alloy (3 runs) | −220 | 366 |
| Cast Vitallium ® Alloy (4 runs) | −223 | 340 |
| FHS ® Vitallium ® Alloy (3 runs) | −174 | 346 |

EXAMPLES 2-5

Four 100 lb batches of alloying ingredients, having the compositions listed hereinafter, were fabricated into solid alloy products in a similar manner according to the following procedure.

Each of the batches was induction-melted and atomized in a nitrogen atmosphere using an apparatus as illustrated schematically in the accompanying drawing.

Each of the atomized powders was screened to −60 mesh then loaded into a mild steel can. The mild steel cans [144.3 mm (4.5 in.) O.D.×101.6 mm (4.0 in.) I.D.] were sandblasted, polished with a flap wheel and purged with the same atomized powder to clean the inside completely. The compacts were evacuated at 204° C. (400° F.) to a leak rate of 10 micron/minute then sealed.

The sealed cans were extruded to 38.1 mm (1.5 in.) diameter using a 1400 ton press. The extrusion conditions were as follows:

| Extrusion Temperature | 1121° C. (2050° F.) |
|---|---|
| Extrusion Ratio | 9:1 |
| Die Size | 38.1 mm (1.5 in.) |
| Lubrication | Oil-base graphite |
| Soaking Time | 4-h at 1121° C. (2050° F.) |

After decanning, the extruded bars were swaged to 16.6 mm (0.655 in.) diameter at 1121° C. (2050° F.) or 1177° C. (2150° F.). The swaged bars were forged to 12.7 mm (0.5 in.)×15.9 mm (0.625 in.) bar products at the same swaging temperatures.

The swaging and forging procedures are as follows:

Swaging

| Size of extruded bar | 32.4 mm (1.275 in.) diameter |
|---|---|
| Annealing | ½ h/871° C. (1600° F.) + 1 h/1121° C. (2050° F.). |
| Swaging Temperature | 1121° C. (2050° F.) and 1177° C. (2150° F.) |
| Reduction | 25% |
| Reheat | After each pass at the swaging temperature |
| Total Reduction | 75% |
| Finish Size | 16.6 mm (.655 in.) |
| No. of pass | 5 |

Forging

| Size of swaged bar | 16.6 mm (.655 in.) |
|---|---|
| Temperature | 1121° C. (2050° F.) and 1177° F. (2150° F.) |
| Die Size | 12.7 mm (.5 in.) × 15.9 mm (.625 in.) |

Room temperature tensile and fatigue tests were then conducted.

The grain structure was studied on both the tensile and fatigue testing samples using a light microscope.

The percentage composition by weight of the alloy in each of the four Examples was as follows:

| Example No. | Co | Cr | Mo | Mn | Si | Al | Ni | Fe | C | O | N | La |
|---|---|---|---|---|---|---|---|---|---|---|---|---|
| 2 | Bal. | 27.24 | 5.97 | .74 | .71 | .45 | .053 | .215 | .09 | .0038 | .21 | .022 |
| 3 | Bal. | 27.27 | 5.97 | .73 | .71 | .55 | .048 | .199 | .09 | .0035 | .26 | —* |
| 4 | Bal. | 27.02 | 6.01 | .75 | .70 | .81 | .187 | .359 | .11 | .0038 | .21 | —* |
| 5 | Bal. | 26.81 | 5.97 | .74 | .70 | .47 | .094 | .520 | .09 | .0142 | .22 | .15 |

*No addition was made

As shown above, the content of the major alloying elements-chromium and molybdenum in each of the four Examples was adjusted to approximately 27.0 wt. % and 6.0 wt. % respectively as in the standard FHS ® Vitallium ® alloy. Example 2 had a similar composition to that of Example 1 aside from its high nitrogen level. Examples 3 and 4 each had a higher aluminum level that Example 2 but no lanthanum. Example 5 had a much higher level of lanthanum than Example 2.

The powder size distributions of the four Examples are similar as shown below:

| Example No. | Screen Analysis, Mesh Size (U.S. Standard %) | | | | | |
|---|---|---|---|---|---|---|
|  | −60/80 | −80/100 | −100/140 | −140/230 | −230/325 | −325 |
| 2 | 22.54 | 14.71 | 15.11 | 15.00 | 15.11 | 14.77 |
| 3 | 17.92 | 14.15 | 17.17 | 19.23 | 14.10 | 14.26 |
| 4 | 22.46 | 15.71 | 17.00 | 15.20 | 12.80 | 12.67 |
| 5 | 21.43 | 13.65 | 14.40 | 16.32 | 15.36 | 17.34 |

Microstructure examination showed that the as-forged GADS alloy with homogeneously distributed dispersoids (oxides and nitrides) had a very fine grain size, ASTM #10 or finer. It was found that the grain size of as-forged GADS alloy was little effected by the forging temperatures 1121° C. (2050° F.) or 1177° C. (2150° F.) or the various lanthanum and aluminum contents.

After a sinter-cycle treatment (2h/1218° C. (2225° F.)+½h/1293° C. (2360° F.), limited grain growth occurred in the GADS alloys. It was found that the grain size of the alloy of Example 5 (ASTM 8-9) having a higher lanthanum content is somewhat smaller than those of Examples 2, 3 and 4 (ASTM #8).

At higher magnification, the dispersoids (oxides and nitrides) were homogeneously distributed in the alloys of Examples 2 and 5. However, aluminum ($Al_2O_3$)

tended to cluster in the grain boundaries of the alloys of Examples 3 and 4. The grain size of post-sinter GADS alloys was not affected by the forging temperatures 1121° C. (2050° F.) vs. 1177° C. (2150° F.). Similar to FHS ® Vitallium ® alloy, deformation twins were also present in the GADS alloys.

MECHANICAL PROPERTIES OF GADS ALLOYS ACCORDING TO THE INVENTION

A. Tensile Properties

The results of tensile tests on the alloys of Examples 1–5 are presented in Tables IV and V below. The 1121° C. (2050° F.) forged alloys exhibited higher strength, either the as-forged or the sinter-cycle treated, than the 1177° C. (2150° F.) forged ones. The stronger strength in the alloys of Examples 2 and 5 compared to the alloys of Examples 3 and 4 was most likely contributed by the lanthanum oxide content. The significant improvement in the strength of the alloy of Example 2 as compared to the alloy of Example 1 was mainly due to its nitride level.

As shown in Table IV, the tensile ductility of as-forged alloys of Example 2 to 5 is much lower than that of the alloy of Example 1. From careful examination on the surfaces of fractured tensile samples, it was found that the samples machined from the alloys of Examples 2 to 5 had deep circumfercial machining marks which would account for the elongation and reduction in area values.

As shown in Table V the alloys of Example 2 to 5 have excelleent post-sinter ductility (46.4–58.7%).

TABLE IV

Tensile Properties of GADS Alloys

| Example No. | Condition | U.T.S. MPa | (ksi) | 0.2% Y.S. MPa | (ksi) | El (%) | RA (%) |
|---|---|---|---|---|---|---|---|
| 1[a][c] | As-forged | 1300.6 | (189.5) | 812.9 | (117.9) | 32.0 | 27.5 |
| 2[a] | As-forged | 1313.5 | (190.5) | 1052.1 | (152.6) | 9.6[d] | 11.6[d] |
| 2[b] | As-forged | 1316.9 | (191.0) | 986.7 | (143.1) | 12.3[d] | 14.0[d] |
| 3[a] | As-forged | 1239.7 | (179.8) | 981.8 | (142.4) | 7.9[d] | 11.0[d] |
| 3[b] | As-forged | 1243.2 | (180.3) | 983.9 | (142.7) | 7.9[d] | 10.9[d] |
| 4[a] | As-forged | 1264.5 | (183.4) | 944.6 | (137.0) | 7.4[d] | 10.1[d] |
| 4[b] | As-forged | 1213.5 | (176.0) | 856.4 | (124.2) | 8.8[d] | 10.9[d] |
| 5[a] | As-forged | 1332.1 | (193.2) | 1016.3 | (147.4) | 11.8[d] | 14.3[d] |
| 5[b] | As-forged | 1216.3 | (176.4) | 877.7 | (127.3) | 7.1[d] | 10.1[d] |

[a]Swaged and forged at 1121° C. (2050° F.).
[b]Swaged and forged at 1177° C. (2150° F.).
[c]Samples were machined from forged hip stems.
[d]The low elongation and reduction in area values were mainly due to the deep circumferential machining marks on test samples.

TABLE V

Tensile Properties of GADS Alloys

| Example No. | Condition | U.T.S. MPa | (ksi) | 0.2% Y.S. MPa | (ksi) | El (%) | RA (%) |
|---|---|---|---|---|---|---|---|
| 1[a][c] | Sinter | 1136.3 | (164.8) | 530.9 | (77.0) | 37.2 | 30.2 |
| 2[a] | Sinter | 1274.9 | (184.9) | 660.5 | (95.8) | 58.7 | 36.2 |
| 2[b] | Sinter | 1242.5 | (180.2) | 580.6 | (84.2) | 54.6 | 36.5 |
| 3[a] | Sinter | 1234.2 | (179.0) | 620.6 | (90.0) | 55.3 | 33.9 |
| 3[b] | Sinter | 1200.4 | (174.1) | 573.0 | (83.1) | 49.2 | 32.9 |
| 4[a] | Sinter | 1229.4 | (178.3) | 579.9 | (84.1) | 50.5 | 33.4 |
| 4[b] | Sinter | 1221.1 | (177.1) | 543.3 | (78.8) | 46.4 | 33.4 |
| 5[a] | Sinter | 1283.8 | (186.2) | 661.2 | (95.9) | 51.0 | 33.2 |
| 5[b] | Sinter | 1254.9 | (182.0) | 614.3 | (89.1) | 51.0 | 34.1 |

[a]Swaged and forged at 1121° C. (2050° F.).
[b]Swaged and forged at 1177° C. (2150° F.).
[c]Samples were machined from forged hip stems.

B. Fatigue Properties
(a) Cantilever Fatigue Properties
The results of cantilever fatigue tests on the GADS alloy of Examples 2 to 5 are present in Table VI:

TABLE VI

Cantilever Fatigue Properties of GADS Alloys

| Example No. | Sample No. | Condition | Stress MPa | (ksi) | Cycles (× 10³) | Results |
|---|---|---|---|---|---|---|
| 2 | (2)-1-1[a] | Sinter | 930.8 | (135) | 10,400 | RO[c] |
|  |  |  | 1034.2 | (150) | 947 | Failed |
|  | (2)-1-2[a] | Sinter | 999.8 | (145) | 7,580 | Failed |
|  | (2)-1-3[a] | Sinter | 999.8 | (145) | 5,600 | Failed |
|  | (2)-2-1[b] | Sinter | 999.8 | (145) | 10,300 | RO[c] |
|  |  |  | 1034.2 | (150) | 327 | Failed |
|  | (2)-2-2[b] | Sinter | 1020.5 | (148) | 3,400 | Failed |
| 3 | (3)-1-1[a] | Sinter | 930.8 | (135) | 3,920 | Failed |
|  | (3)-1-2[a] | Sinter | 930.8 | (135) | 14,900 | RO[c] |
|  |  |  | 965.3 | (140) | 9,400 | Failed |
|  | (3)-2-1[b] | Sinter | 965.3 | (140) | 270 | Failed |
|  | (3)-2-2[b] | Sinter | 930.8 | (135) | 10,200 | RO[c] |
|  |  |  | 965.3 | (140) | 10,300 | RO[c] |
|  |  |  | 999.8 | (145) | 15,500 | RO[c] |
|  |  |  | 1034.2 | (150) | 1,030 | Failed |
| 4 | (4)-1-1[a] | Sinter | 930.8 | (135) | 669 | Failed |
|  | (4)-1-2[a] | Sinter | 827.4 | (120) | 10,200 | RO[c] |
|  |  | Sinter | 896.4 | (130) | 10,400 | RO[c] |
|  |  | Sinter | 965.3 | (140) | 456 | Failed |
|  | (4)-2-1[b] | Sinter | 896.4 | (130) | 10,000 | RO[c] |
|  |  | Sinter | 930.8 | (135) | 10,000 | RO[c] |
|  |  |  | 965.3 | (140) | 562 | Failed |
| 5 | (5)-1-1[a] | Sinter | 930.8 | (135) | 10,300 | RO[c] |
|  |  |  | 999.8 | (145) | 10,300 | RO[c] |
|  | (5)-1-2[a] | Sinter | 1034.2 | (150) | 5,900 | Failed |
|  | (5)-2-1[b] | Sinter | 1034.2 | (150) | 1,980 | Failed |
|  | (5)-2-2[b] | Sinter | 1020.5 | (148) | 9,800 | Failed |

Notes:
[a]forged at 1121° C. (2050° F.).
[b]forged at 1177° C. (2150° F.).
[c]RO = run out - No failure up to 10⁷ cycles The above data indicate that the different forging temperatures 1121° C. (2050° F.) 1177° C. (2150° F.) had little effect on the cantilever fatigue properties of the alloy. Also, the alloys of Examples 2 and 5 have stronger strength than the alloys of Examples 3 and 4. The fatigue strength of the alloy of Example 5 is slightly stronger than that of Example 2. The only significant difference between these two alloys is that the alloy of Example 5 has a higher lanthanum content than that of Example 2. The alloy of Example 4 has lower strength than that of Example 3. X-ray EDS analysis on the GADS alloy showed that aluminum ($Al_2O_3$) tends to cluster in the grain boundaries of Example 3 and 4. The continuous $Al_2O_3$ in the grain boundaries could be prone to initiate a fatigue crack, therefore, further reducing the strength of the alloy of Example 4.

The fatigue strength of GADS alloys is summarized in Table VII.

TABLE VII

Post-Sinter Fatigue Strength of GADS Alloys[3]

| Example No. | Cantilever[1] MPa | (ksi) | Rotating Beam[2] MPa | (ksi) |
|---|---|---|---|---|
| 1 | 931 | (135) | 483 | 70 |
| 2 | 965–1000 | (140–145) | 621 | 90 |
| 3 | 931–965 | (135–140) | 621 | 90 |
| 4 | 896–931 | (130–135) | 621 | 90 |
| 5 | 1000–1034 | (145–150) | 621 | 90 |

Notes:
[1] Data obtained from both the 1121° C. (2050° F.) and 1177° C. (2150° F.) forged samples.
[2] Data obtained from the 1121° C. (2050° F.) forged samples.
[3] At $10^7$ cycles.

The data in Table VII indicate that the alloys of Examples 2 and 5 are stronger than those of Examples 3 and 4.

The fatigue strength of the alloy of Example 2 is significantly greater than that of Example 1. This result demonstrates that nitrogen (nitrides) can increase the post-sinter fatigue strength of the GADS alloy.

Rotating beam fatigue data of the alloys of Example 2 and 5 compared with those of cast and FHS ® Vitallium ® alloy are listed in Table VIII. The post-sinter fatigue strength of the alloy of Example 2 is much higher than those of cast and FHS ® Vitallium ® alloy. This corresponds to approximately 125% strength improvement over the cast Vitallium ® alloy.

TABLE VIII

Rotating Beam Fatigue Properties of GADS, Cast and FHS ® Vitallium ® Alloys

| | Fatigue Strength at $10^7$ cycles | |
|---|---|---|
| | MPa | (ksi) |
| Cast Vitallium ® Alloy | | |
| Solution Heat Treated | 414 | (60) |
| Sinter Cycle Treated | 276 | (40) |
| FHS ® Vitallium ® Alloy | | |
| As-forged (1950° F.) | 758 | (110) |
| Sinter-cycle Treated | 324 | (47) |
| GADS Alloy (Examples 2 and 5) | | |
| As-forged | 758 | (110) |
| Sinter Cycle Treated | 621 | (90)* |

*This low drop in fatigue strength after heat treatment (sintering), as compared to that for FHS ® Vitallium ® alloy demonstrates, the exceptional retention of strength achieved by the alloys of the invention.

We claim:

1. A prosthesis made by forging a high-strength, corrosion-resistant, high temperature stable, ductile alloy having homogeneously distributed dispersed oxides and fine, equiaxed grain structure after high temperature exposure, said alloy being produced by gas atomisation and consisting essentially of the following percentage composition by weight:

| | |
|---|---|
| chromium | 26 to 30 |
| molybdenum | 5 to 7 |
| manganese | 0 to 1 |
| silicon | 0 to 1 |
| iron | 0 to 0.75 |
| nickel | 0 to 1.0 |
| carbon | 0 to 0.35 |
| nitrogen | 0 to 0.25 |
| oxygen | 0.003 to 0.20 |
| oxide-forming metal | 0.003 to 2.0 | and the balance cobalt, apart from trace amounts of incidental impurities; in which the oxide-forming metal is a metal selected from the group consisting of magnesium, calcium, aluminum, yttrium, lanthanum, titanium and zirconium, which forms high temprature-stable, non-accretive, fine oxide particles which oxide has a free energy of formation greater than the oxide of the matrix metal and is homogeneously distributed in the dispersed phase; and said alloy after fabrication by gas atomization, thermomechanical processing and further high temperature exposure has an ultimate tensile strength of 160-200 k.s.i., a 0.2% offset yield strength of 75-100 k.s.i., an elongation of 37 to 60%, and a fatigue strength at $10^7$ cycles of 70-95 k.s.i.

2. A prosthesis accordindg to claim 1, in which the oxide forming metal of the forged alloy is aluminum, lanthanum or a mixture thereof.

3. A prosthesis according to claim 2, in which the percentage composition by weight of the forged alloy is:

| | |
|---|---|
| chromium | 26.47–27.27 |
| molybdenum | 5.50–6.01 |
| manganese | 0.73–0.78 |
| silicon | 0.70–0.71 |
| iron | 0.066–0.359 |
| nickel | 0.002–0.187 |
| carbon | 0.09–0.11 |
| nitrogen | 0.10–[0.26]0.25 |
| oxygen | 0.0035–0.016 |
| aluminum | 0.40–0.81 |
| lanthanum | 0–0.15 | and the balance cobalt, apart from trace amount of incidental impurities.

4. A prosthesis according to claim 2, in which the percentage composition by weight of the forged alloy is:

| | |
|---|---|
| chromium | 27.24 |
| molybdenum | 5.97 |
| manganese | 0.74 |
| silicon | 0.71 |
| iron | 0.215 |
| nickel | 0.053 |
| carbon | 0.09 |
| nitrogen | 0.21 |
| oxygen | 0.0038 |
| aluminum | 0.45 |
| lanthanum | 0.022 | and the balance cobalt, apart from trace amount of incidental impurities, and said alloy after fabrication by gas atomisation, thermomechanical processing and further high temperature exposure has an elongation of 58.7%.

5. A prosthesis according to claim 2, in which the percentage composition by weight of the forged alloy is:

| | |
|---|---|
| chromium | 26.81 |
| molybdenum | 5.97 |
| manganese | 0.74 |
| silicon | 0.70 |
| iron | 0.52 |
| nickel | 0.094 |
| carbon | 0.09 |
| nitrogen | 0.22 |
| oxygen | 0.0142 |
| aluminum | 0.47 |
| lanthanum | 0.15 | and the balance cobalt, apart from trace amounts of incidental impurities, and said alloy after fabrication by gas atomisation, thermomechanical processing and further high temperature exposure has an elongation of 51.0%.

6. A prosthesis according to claim 1 having a porous coating.

* * * * *